United States Patent
Eberle

(10) Patent No.: US 7,744,821 B2
(45) Date of Patent: Jun. 29, 2010

(54) BLOOD BAG CUP FOR CENTRIFUGES

(75) Inventor: Guenter Eberle, Tuttlingen (DE); Liese Eberle, legal representative, Tuttlingen (DE)

(73) Assignee: Andreas Hettich GmbH & Co. KG, Tuttlingen (DE)

( * ) Notice: Subject to any disclaimer, the term of this patent is extended or adjusted under 35 U.S.C. 154(b) by 911 days.

(21) Appl. No.: 11/231,044

(22) Filed: Sep. 20, 2005

(65) Prior Publication Data

US 2006/0062697 A1  Mar. 23, 2006

(30) Foreign Application Priority Data

Sep. 21, 2004  (EP) ................................. 04022381
Nov. 24, 2004  (DE) ....................... 10 2004 056 620

(51) Int. Cl.
  B01L 99/00  (2010.01)
  B01L 3/00  (2010.01)
  B01L 9/00  (2010.01)
  B01D 33/327  (2006.01)
  B65D 6/00  (2006.01)
  B65D 6/18  (2006.01)

(52) U.S. Cl. ....................... 422/104; 422/101; 422/102; 422/103; 210/767; 210/782; 220/4.06; 220/4.07

(58) Field of Classification Search ................. 422/101, 422/102, 103, 104; 210/767, 782; 220/4.06, 220/4.07

See application file for complete search history.

(56) References Cited

U.S. PATENT DOCUMENTS

| 4,447,220 A | * | 5/1984 | Eberle | ............................. 494/26 |
| 4,539,005 A | | 9/1985 | Greenblatt | |
| 4,582,606 A | * | 4/1986 | McCarty | ........................ 210/516 |
| 5,158,749 A | | 10/1992 | Eberle | ............................. 422/102 |

FOREIGN PATENT DOCUMENTS

| EP | 0 278 043 | 8/1988 |
| EP | 0 386 558 | 12/1990 |
| EP | 0 416 495 | 3/1991 |
| EP | 0 386 558 | 9/1993 |
| WO | 92/00145 | 1/1992 |

OTHER PUBLICATIONS

EP0278043, Aug. 1988, Eberle, Gunter, Machine Translated Version.*
"Zentrifugation in kleinen and grossen Zellkulturflaschen", Zellkulturtechnik, Jan. 2004.

* cited by examiner

*Primary Examiner*—Jill Warden
*Assistant Examiner*—Dean Kwak
(74) *Attorney, Agent, or Firm*—Baker & Daniels LLP

(57) ABSTRACT

A blood bag cup, which is designed as a double cup with two individual cups with two separate chambers, one for accommodating the withdrawal and inflation bag and one for accommodating the satellite bag. The respective chamber for the satellite bags is preferably jointed. Advantages are an extremely high separation efficiency factor with maximum plasma yield with pure plasma and more than 50% time savings based on the doubled design of the double-chambered double cup.

9 Claims, 1 Drawing Sheet

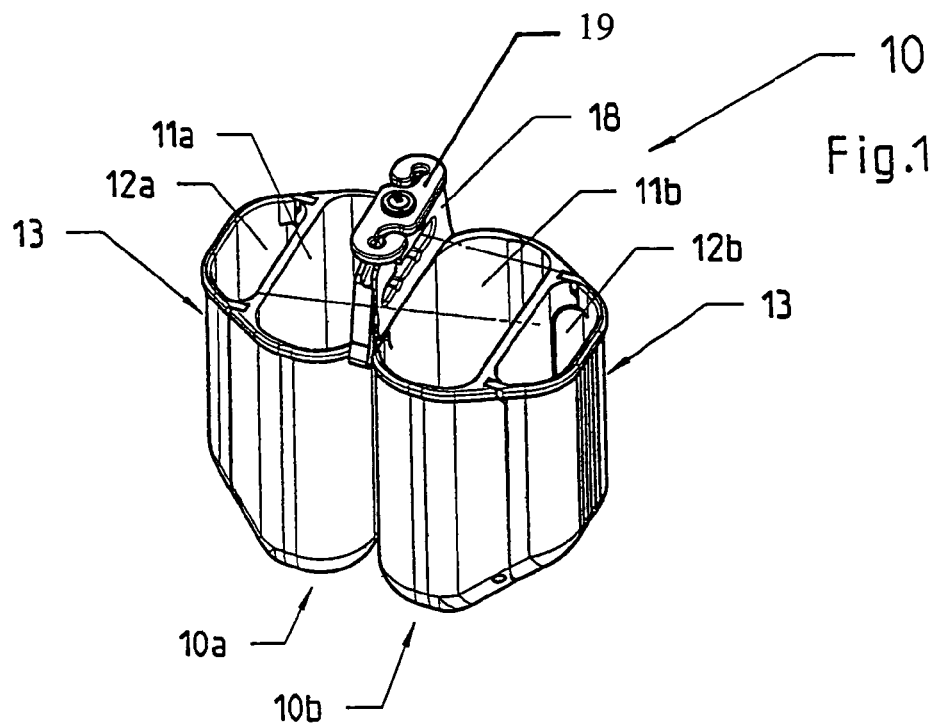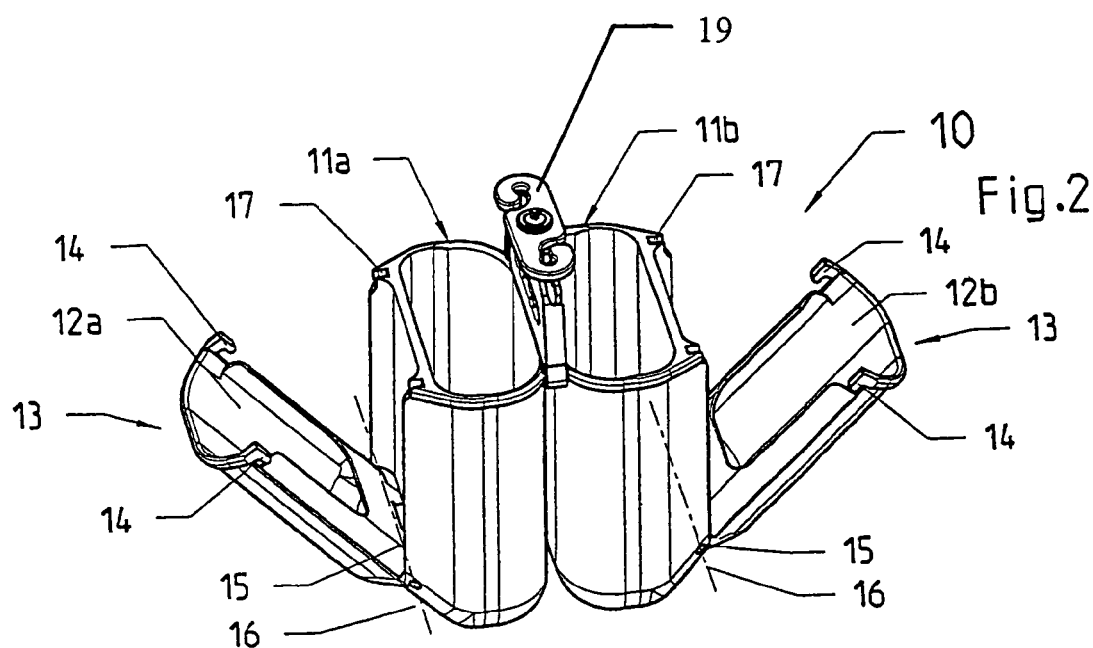

BLOOD BAG CUP FOR CENTRIFUGES

The invention relates, in particular, to a hinged blood bag cup for centrifuges.

A hinged cell culture bottle adapter for use in cups for centrifuges, which is split into two or three parts and is hinged on the bottom along a horizontal axis, became known from the periodical entitled "Zellbiologie" (Cell Biology), Edition 1/2004, pages 28 and 29. This should prevent siphoning from the cell culture bottle into a centrifuge tube and vice verse, which leads to lower risk of contamination, efficient cell cultivation and less time, work and laboratory material. Due to the hinged nature, an undesired mixing of the separation layer of the components separated during centrifugation is reduced or even avoided. However, this cell culture bottle cup fulfills only one static purpose, namely enclosing an inherently solid form of a cell culture bottle, which is rectangular in cross-section, and holding this cell culture bottle in a form-fitting manner in the adapter. One application of this adapter for use in cups for centrifuges with flexible blood bags is not provided and is also not possible. Moreover, a maximum of two chambers are provided so that at least the same time effort is needed in comparison with conventional double cups, which are described below.

As a further state of the art, a conventional, flexible withdrawal bag filled with blood/blood components and a satellite bag for collecting a separated blood component and, if necessary, a nutrient solution bag connected with it via a connection tube is assumed, whereby the bags are used together in a conventional, unhinged (double) blood bag cup and centrifuged. Then the bags are removed from the cup and hung open individually in a pressing device, and the blood components are separated from one another through pressing. The disadvantage hereby is that, during centrifugation, the bags are pressed together and into the wall of the cup strongly (in particular to the floor of the cup) and, after centrifugation during removal of the bags from the cups and during separation of the bags from each other, a relatively strong force and skillfulness must be used, which leads to a risk of damage to the bags and tubes and to a relatively strong, undesirable agitation of the withdrawal bag and thus the separation layer between the separated blood components. The separated blood components in the area of the separated layer thereby partially mix together again and the volume ratio of the separated blood components to each other changes, i.e. the separation efficiency factor decreases undesirably. Another disadvantage is that the bags, in particular when not completely full, do not fit optimally in the cup and thus fold and can form sedimentation nests during centrifugation.

A hinged blood bag cup for centrifuges that is separated into two parts by two shell halves and can be opened on the side along a vertical axis, in particular in the form of a film joint, became known from EP-A 0 386 558. A blood bag, which is connected with at least one other blood bag within the centrifuge via connection tubes, can be inserted into the functional cup. Furthermore, a displacement body, which can change the volume of the functional cup, next to the functional cup can be inserted into functional cup. A holder for the blood bag that can be inserted between these shell halves is arranged on the top side of the shell halves of the functional cup. The aforementioned disadvantages of the state of the art of the unhinged blood bag cup for centrifuges is partially avoided by the hinged blood bag cup for centrifuges of EP-A 0 386 558; however, the withdrawal and satellite bags belonging to each other are inserted into one blood bag cup or into two different blood bag cups. If the withdrawal and satellite cups belonging together are provided in a common blood bag cup, then the bags in turn are pressed together during centrifugation such that an undesired mixing of separated components cannot be avoided in the withdrawal bag even when the blood bag cup is open. If the withdrawal and satellite bags belonging together are provided in two different blood bag cups, then a pressing together during centrifugation is reliably prevented; however, free space in the blood bag cups for withdrawal bags within a centrifuge is unnecessarily occupied by the satellite bags and it takes four times as long compared to conventional double cups.

Thus, the object of this invention is to further develop the blood bag cup such that, for one, a higher separation efficiency factor is achieved, as with the hinged cups, and, on the other hand, as many withdrawal bags and thus the highest possible blood volume can be collected within the centrifuge, as with double cups.

It is hereby important that a special double cup with two individual cups, each with a double chamber, is provided, whereby at least one withdrawal bag and at least one inflation bag can be inserted into the one chamber of each of the two individual cups and at least one associated satellite bag for the separated blood plasma (and if necessary for a nutrient solution to be fed to the withdrawal bag) connected with the respective withdrawal bag can be inserted into the other chamber of each of the two individual cups.

The advantages of the blood bag cup are an extremely high separation efficiency factor with e.g. maximum plasma yield, with pure plasma and more than 50% time savings based on the doubled design of the double-chambered double cup.

For the separation of blood components located in the bags, it is important for the cups that it is designed as a double-chambered double cup with two cups and each cup is designed with two separated chambers, one for the withdrawal and inflation bag and one for the satellite bag.

The two cups are, in particular, mirror images of each other and are permanently attached to each other via a handle.

The two chambers of the two cups of the double cup for the withdrawal and inflation bag preferably lie next to each other directly or indirectly, and the chambers for the satellite bag are arranged further away from each other.

The respective chamber for the satellite bag is preferably hinged and adjustable so that a chamber flap is attached to the cup via a hinge. In particular, the hinge axis lies horizontal in the cup, but can also lie vertically.

There is preferably an, in particular, rotatable tube-guide part arranged between the adjacent chambers of the double cup, which simultaneously serves as a guide for the connection tube between the bags during the centrifugation and during the pressing (separation of the blood components in the device), which give the connection tubes a vertical alignment.

Furthermore, check valves for the admission of compressed air are preferably arranged in the area of the handle, preferably below it.

In contrast to the previously conventional pressing devices, which come after conventional blood centrifugation, double the amount, namely two blood bags, can be pressed at one time, which cuts the processing time in half.

Furthermore, as with previous conventional double-chambered cups, the blood bags do not need to be removed from the centrifuge cups and hung open and individually in a pressing device. The previously necessary withdrawal of the cups required jerking, because the blood bags were pressed very firmly and free of air into the cups. This is no longer the case with double-flap cups according to the invention; the bags remain inside. Even with the most careful work, the state of the art cannot reliably avoid a whirling, i.e. the mixing of the boundary layers of the sediments.

In the double-flap cup according to the invention, two independently attached empty air bags are attached below the handle, which are supplied with compressed air before (optional) and after (obligatory) centrifugation. The supply of compressed air is applied before centrifugation, in order to press the blood bags tight and to avoid wrinkling with sedimentation nests. The air connection at the handle has two check valves, which maintain the air pressure in the inflation bags during the separation of the compressed-air source. After centrifugation, the supply of compressed air serves to press out a separated blood component.

The satellite bags, i.e. as a rule an empty bag for the plasma and another one with up to 110 ml of nutrient solution for the remaining erythrocyte concentrate as well as the connection tubes, are comfortably placed in the lateral flap parts, which can be closed for centrifugation and can be opened after centrifugation, in order to ensure easy handling. Even the satellite bags tend to settle in the direction of the ground. Removal from the opened cups is thus much easier and hassle-free.

The flap parts themselves have a joint with a slot on the bottom and two longitudinal hooks on both sides, with which they are simply pushed downwards for a force-fit closure and upwards for opening.

A wing that can be pivoted 90°, which is parallel to the bags for the filling in the longitudinal direction and is turned by 90°, i.e. is aligned perpendicular to the bags, in order to hold the connection tube perpendicular to the satellite bag and to prevent twisting, is attached above the handle.

When using conventional separators/pressing devices, the centrifuged preserves must at least be removed from the centrifuge cups and attached to the pressing device. The sediment can thereby be whirled up again. The device according to the invention directly presses out the preserves in the centrifuge cups, without needing to remove the extremely full bag.

Advantages: pressing occurs directly in the centrifuge inserts. No whirling up of the sediments through the removal of the bag from centrifuge inserts after centrifugation. Pure plasma. Easier handling. Saves time: 2 preserves are pressed out at the same time. Saves space: compact construction. Requires little space compared to conventional separators. Maximum plasma yield.

The present invention involves, in particular, immobilizing to the greatest extent possible a known soft blood bag, which avoids wrinkling from the very start, in order to prevent the formation of sediments in the folds. For this, the filled blood bag is placed in the application cups, which is provided with an empty air bag on the inside. The hinged side cup accommodates the satellite bags and tubes of the blood-bag system and is closed with the hinged partition, whereby a compact, closed cup half or application half is created, which is connected with a second half via a handle, whereby a double-cup blood bag insert is created. With the help of an air pump, the two air bags can be easily pumped up until the blood bag no longer has any folds. Then, the double inserts are placed in the metal cups of the centrifuge for centrifugation.

During centrifugation, the air in the air bag is displaced and forms an air bubble, which stabilizes the connection pieces of the tubes and prevents twisting, which also prevents the formation of unwanted sedimentation.

The connection tubes can also be trimmed to the vertical position when leaving the blood bag via floating stabilization brackets, which also and additionally prevents twisting and sedimentation. However, this is not necessary due to the pivotable wings.

After centrifugation, the doubled application cups are removed from the centrifuge with their contents, the two side cups are opened and the satellite bags hanging on the connection tubes are taken out.

At the same time, both air bags are pumped up further via an air pump and the plasma remaining in the blood bag is displaced into the satellite bags, as it can exactly be done for the extraction of pooled thrombocytes.

Advantage: The centrifuged blood bag does not need to be pulled out of its repository gently or forcibly, which more or less causes remixing; rather the components remain intact up to the disconnection with largely sharp dividing lines.

A disagreeable wrinkling and twisting of the connection pieces, especially in under-filled bags, is avoided.

Below, the invention is described in greater detail using drawings representing only one embodiment. Further characteristics and advantages of the invention come from the drawings and their descriptions.

The drawings show the following:

FIG. 1: A perspective view of a closed blood bag cup according to the invention;

FIG. 2: A perspective view of an open blood bag cup according to the invention and in accordance with FIG. 1.

FIGS. 1 and 2 show a double-flap cup 10 according to the invention, in the closed position (FIG. 1) and in the open position (FIG. 2) with opened flap parts 13.

The double-flap cup 10 according to the invention is made up of two cups 10*a*, 10*b*, which are attached to each other as directly or indirectly as mirror images of each other, permanently or temporarily, via a handle 18 with its chambers 11*a*, 11*b* for the withdrawal and inflation bags. One chamber 12*a*, 12*b* for the satellite bags, each of which have a hinged flap part 13, is attached to the respective chamber 11*a*, 11*b* for the withdrawal and inflation bag. This flap part 13 is swivel-mounted along an axis 16 via a hinge 15 with the rest of the chamber 12*a*, 12*b*, which in turn is connected with the chamber 11*a*, 11*b*. The flap part 13 is secured when closed by hook 14, which snap into the assigned collets 17. As shown in FIG. 2, each flap part 13 has a cutout in the upper portion thereof that faces its respective first chamber 11*a* and a retaining portion below the cutout shown as a wall adapted to hold the satellite bag when inserted in the second chamber.

All chambers 11, 12 are open on the top and closed on the bottom so that the respective bags are easy to insert.

Above the handle 18, a tube guide wing 19, which is designed in a pivotable manner in a horizontal plane, is arranged in a pivotable manner around a vertical axis. The connection tubes (not shown) between the withdrawal and the satellite bags (not shown) are held in an advantageous vertical position by the hook-shaped ends of the tube guide part 19 with curved openings, so that an optimal, unhindered fluid flow is enabled during the pressing out of the blood components to be separated, but also for the prevention of the embedding of nests of unseparated blood components (e.g. erythrocyte nests).

If the double cup 10 is connected with a pressing device (not shown), then the connections (not shown) for the air supply of the inflation bags are coupled with check valves (not shown) of the individual cups 10*a*, 10*b*, whereby these check valves are connected with the inflation bags (not shown) in the inside chambers 11*a*, 11*b* of the individual cups 10*a*, 10*b*.

Before centrifugation, the inflation bags are pumped up with a low initial pressure in order to compactly press the withdrawal and inflation bags into the chambers 11*a*, 11*b*. After centrifugation, the inflation bags are pumped up with a higher final pressure in order to finally separate the centrifuged blood components from each other, in that a part is squeezed out of the withdrawal bag by means of the inflation bag.

| Figure Legend |
| --- |
| 10. Double cup; |
|    10a First individual cup; |
|    10b Second individual cup; |
| 11. Of 12 separated chambers for withdrawal bag and inflation bag; |
|    11a for the first individual bag; |
|    11b for the second individual bag; |
| 12. Hinged chamber for accommodating the satellite bag |
| 13. Flap part from 12 |
| 14. Hook from 12 |
| 15. Joint between 11 and 12 |
| 16. Axis from 15 |
| 17. Collets from 14 |
| 18. Handle |
| 19. Tube guide wings, pivotable 90° with snapping |

The invention claimed is:

1. A blood bag double cup assembly for separating blood components contained in bags, comprising:

first and second interconnected single cups;

each of said single cups comprising two separate chambers connected to and adjacent to each other, the first of said chambers adapted for receiving collection and inflatable bags and the second of said chambers adapted for receiving satellite bags, said first and second chambers being open at the top to allow insertion of the respective bags into the chambers from above;

each of the second chambers being formed as a flap pivotally mounted lo its single cup via a hinge such that said flap is pivotable about an axis relative to the first chamber of its single cup while connected to such first chamber, the flap having a cutout in an upper portion thereof facing its respective first chamber and a retaining portion below the cutout in the lower portion of the flap adapted to hold a satellite bag when inserted in the second chamber;

the first chamber being positioned adjacent to each other and the second chambers being positioned away from each other outside of the first chambers such that said chambers are arranged in the following sequence side by side: the second chamber of the first single cup, the first chamber of the first single cup, the first chamber of the second single cup, the second chamber of the second single cup;

the first and the second cup with their respective first and second chambers are located next to each other as mirror images.

2. The cup assembly of claim 1, further comprising a pivotable tube guide wing located between the adjacent collection/inflation bag chambers and which is adapted to guide connection tubes into vertical alignment.

3. The cup assembly of claim 2, wherein the interconnected single cups are mirror images of one another.

4. The cup assembly of claim 3, wherein the interconnected single cups are attached to each other by a handle.

5. The cup assembly of claim 1, wherein the interconnected single cups are mirror images of one another.

6. The cup assembly of claim 5, wherein the interconnected single cups are attached to each other by a handle.

7. The cup assembly of claim 1, wherein the interconnected single cups are attached to each other by a handle.

8. The cup assembly of claim 2, wherein the interconnected single cups are attached to each other by a handle.

9. The cup assembly of claim 3, wherein the interconnected single cups are attached to each other by a handle.

* * * * *